United States Patent [19]

Kaneko et al.

[11] Patent Number: 5,273,639
[45] Date of Patent: Dec. 28, 1993

[54] PROBE ELECTRODE

[75] Inventors: Hiroko Kaneko; Ken Nozaki; Akira Negishi, all of Tsukuba, Japan

[73] Assignees: Agency of Industrial Science & Technology; Ministry of International Trade & Industry, Tokyo, Japan

[21] Appl. No.: 905,238

[22] Filed: Jun. 29, 1992

Related U.S. Application Data

[63] Continuation of Ser. No. 549,240, Jul. 9, 1990, abandoned, which is a continuation of Ser. No. 325,291, Mar. 17, 1989, abandoned.

[30] Foreign Application Priority Data

Mar. 31, 1988 [JP] Japan .................................. 63-78698
Mar. 31, 1988 [JP] Japan .................................. 63-78699

[51] Int. Cl.$^5$ .......................................... G01N 27/30
[52] U.S. Cl. ...................................... 204/400; 204/294
[58] Field of Search ................................ 204/294, 400

[56] References Cited

U.S. PATENT DOCUMENTS

| | | | |
|---|---|---|---|
| 3,838,188 | 9/1974 | Farrell, Jr. ...................... | 264/29.6 X |
| 4,221,773 | 9/1980 | Tsukagoshi et al. ............... | 423/445 |
| 4,226,633 | 10/1980 | Asano et al. ..................... | 264/29.6 X |
| 4,330,387 | 5/1982 | Astruc et al. .................... | 204/294 X |
| 4,511,442 | 4/1985 | Pellergri ......................... | 204/294 X |
| 4,536,272 | 8/1985 | Blanchart et al. ................. | 204/294 |
| 4,551,220 | 11/1985 | Oda et al. ........................ | 204/294 |
| 4,554,063 | 11/1985 | Braun et al. ..................... | 204/294 X |
| 4,596,669 | 6/1986 | Kleiner et al. ................... | 264/105 X |
| 4,775,455 | 10/1988 | Chandramouli et al. .......... | 264/29.1 X |
| 4,814,307 | 3/1989 | Funabashi et al. .............. | 204/294 X |

Primary Examiner—Nam Nguyen
Attorney, Agent, or Firm—Oblon, Spivak, McClelland, Maier & Neustadt

[57] ABSTRACT

A method of making a probe electrode includes the steps of kneading a mixture of 75-80% by weight of a carbon material, 10-14% by weight of an organic binder and 7-9% by weight of mineral oil, forming the kneaded mixture into a predetermined shape, heating the shaped mixture in air the temperature of up to 300° C. and raising the temperature in an atmosphere of inert gas up to 1000° C.

18 Claims, 8 Drawing Sheets

PROBE ELECTRODE

This application is a continuation of application Ser. No. 078/549,240, filed on Jul. 9, 1990, now abandoned, which is also a continuation of Ser. No. 07/325,191, filed Mar. 17, 1989 also abandoned.

BACKGROUND OF THE INVENTION

1 Field of the Invention

The present invention relates to probe electrodes for use in apparatuses for electroanalysis, current-potential measuring, electrolysis reaction and the like and a method of producing the same.

2 Prior Art Statement

In the aforementioned apparatuses, a new electrode surface has to be used each time a different measurement or reaction is conducted to ensure an accurate electrode reaction.

Mercury drop-feed electrodes are well known as electrodes for such applications. In the mercury drop-feed electrode, an insulating slender pipe is filled with mercury and the mercury present at the tip of the slender pipe serves as an electrode. The mercury used as an electrode at the tip of the slender pipe is dropped each time a different measurement or reaction is conducted. This arrangement is extremely convenient because a hew electrode surface is readily obtainable. However, mercury is usable as an electrode on only the negative side since its elution potential is approximately $+0.27$ V. Because of its strong toxicity, moreover, the waste electrode thus dropped has to be recovered for treatment. For this reason, there has developed a demand for a new electrode as a substitute for mercury in consideration of the problem of environmental pollution, which is severely regulated law.

On the other hand, gold or platinum electrodes, or carbon electrodes of graphite or amorphous carbon prepared from sintered carbon material are employed on the positive potential side. Notwithstanding, the gold or platinum electrode is expensive and has to be electrochemically washed in a nitric acid solution to obtain a new electrode surface. In the case of the carbon electrode, it is necessary to carry out the troublesome process of mechanically polishing the surface to obtain a new electrode surface or of electrolytically oxidizing the surface at a very high positive potential. The carbon electrode has additional disadvantages in that it is not only vulnerable to mechanical shock but also insufficient in mechanical strength since it is a sintered material. A strong electrode in the form of a needle that can be thrust into an object being examined is consequently unavailable and, if a binding material like clay is mixed with the carbon material to increase the mechanical strength, the mixture may act as what arrests the electrode reaction. Such an electrode is therefore unusable for accurate reaction measurement.

OBJECT AND SUMMARY OF THE INVENTION

An object of the present invention is to provide a carbon electrode having high mechanical strength, offering accurate electrode reaction with excellent reproducibility and a new electrode surface with ease and a method of producing the same.

In order to accomplish the foregoing object, the present invention provides a method of producing a carbon electrode comprising kneading a mixture of a carbon material, an organic binder and mineral oil, giving the mixture a predetermined shape by extrusion molding, and calcining the resulting mold at high temperatures.

The carbon electrode thus obtained is similar to the lead of a mechanical pencil in view of material quality and embodies the following features: it can cause a stable electrode reaction with excellent reproducibility since it is made of substantially pure carbon material; it can readily be provided in needle-shape since it has high mechanical strength; impurities formed thereon can easily be removed merely by wiping the electrode surface when a new electrode surface is needed; and, in the case of a needle-shaped electrode, a new electrode surface is instantly obtained by fitting the electrode into a tubular case with its front end formed into a thinner pipe, cutting the electrode portion projected from the front end each time a reaction is terminated, and sliding a new electrode out of the case to replace the used one.

Other objects and features of the invention will become apparent from the following description of embodiments with reference to the accompanying drawings.

BRIEF DESCRIPTION OF THE DRAWINGS

FIG. 9(*b*) is a cyclic voltammogram of iron chloride in an electrolyte examined by a platinum electrode.

DESCRIPTION OF THE PREFERRED EMBODIMENT

Figure 1:
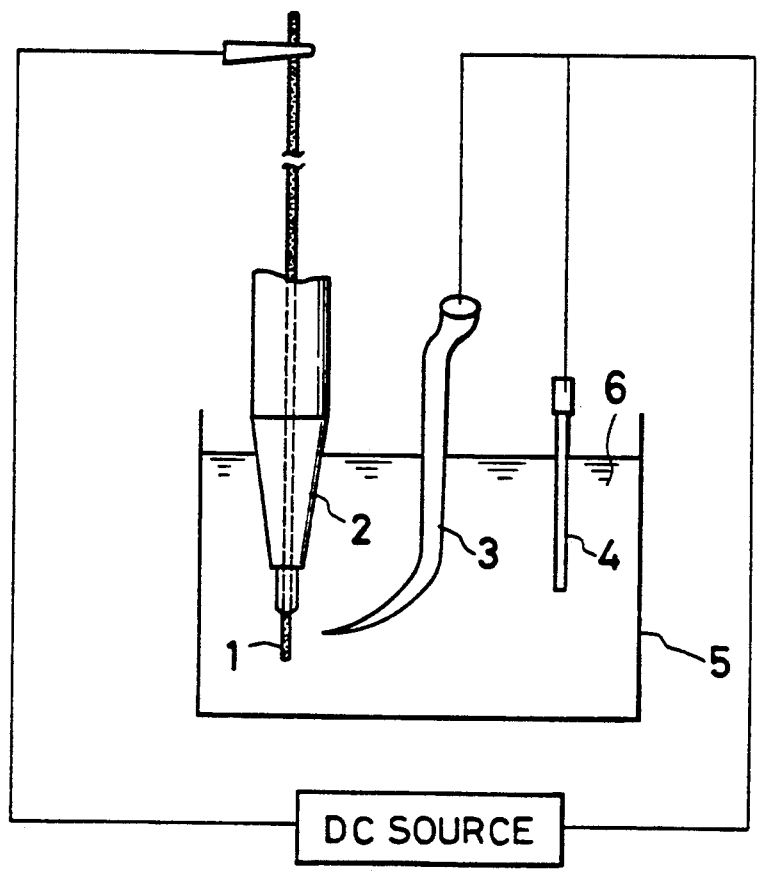
FIG. 1 is a diagram illustrating the implementation of an electrochemical reaction by means of an electrode embodying the present invention.

The present inventors strove to develop a probe electrode as a substitute for the mercury electrode employed in electroanalysis apparatuses or voltammetric measuring apparatuses and the like and completed the present invention based on their discovery of the fact that the carbon material obtained through a method similar to what is employed to manufacture leads for mechanical pencils and made of substantially pure carbon can be suitably used for making such a probe electrode and that the probe electrode thus prepared induces a stable electrode reaction and has not only high mechanical strength but also properties enabling it to be readily molded into any given shape.

More specifically, the probe electrode according to the present invention is made by kneading a mixture of a carbon material, an organic binder and mineral oil, molding the mixture into a predetermined shape, and calcining the result at high temperatures. When the calcined product has gaps or pores large enough to permit entrance of an electrolyte, it is preferably impregnated with silicone, petroleum jelly or the oils.

Graphite, amorphous carbon and the like are usable as the above-described carbon material according to the present invention. Natural graphite containing no heavy metals is especially preferred. The organic binder is used to firmly bind the carbon material, whereas the mineral oil is used to mix the binder with the carbon material uniformly.

As the organic substance used as the organic binder there is employed one which enables the carbon to be retained when it is calcined in an inactive or nonoxidizing atmosphere. More specifically, use can be made of thermoplastic resins such as vinyl acetate resin and polyethylene resin; initial condensation products such as phenol resin and epoxy resin; known organic substances such as coal tar pitch, asphalt, cellulose and lignin derivatives. Among these, vinyl acetate resin and epoxy or phenol resin are preferable.

Any kind of mineral oil is usable as the mentioned mineral oil as long as it contains no heavy metal. A heavy metal, if contained, may affect the results of analysis. Spindle or silicone oil falls under this category.

In addition, a plasticizer such as DOP, DBP, DBS and BPBG is added, if necessary. The compounding ratio of the above-named materials is as follows: 75–85 wt % carbon material; 12–13 wt % organic binder; and approximately 8 wt % mineral oil. These materials should be kneaded sufficiently to wet the surface of the carbon material with the mineral oil. Simultaneously, a strong shearing force is applied thereto, which results in increasing the affinity of the carbon material for the organic binder and therefore the binding strength. The mixture thus prepared by sufficiently kneading the materials is molded into a cylinder, square pillar or any one of the cylindrical, spherical or ringlike form as desired, and calcined. Any known means may be employed for molding purposes; e.g., an extruding machine is used when thin bar-like electrodes are manufactured and a granulating machine is used when spherical electrodes are manufactured. As for calcination, the temperature is raised at the rate of 10° C./hr from room temperature up to 300° C. in air; and at the rate of 30° C./hr from 300° C. up to 1,000° C. in an atmosphere of inert gas, e.g., nitrogen gas. The mixture is then continuously calcined for approximately one hour after 1,000° C. is reached. The rate of raising the temperature during the process of calcination is properly determined, depending on the kind of binder used. When a binder such as a thermoplastic resin or coal tar pitch is used, the temperature is normally raised slowly within the range of 100°–300° C. to have the crosslinking reaction develop while accelerating the dehydrogenating reaction below the melting point of the binder in air since such a binder softens and becomes liquified as it is heated.

When a plasticizer is added, moreover, the mixture is sufficiently calcined at approximately 180° C. in air and the temperature is raised after the plasticizer is removed.

As set forth above, the carbon material, the organic binder and the mineral oil containing no heavy metal are sufficiently kneaded and molded into a predetermined form and then calcined at high temperatures to provide the probe electrode according to the present invention, the mixture being molded after the carbon material and the organic binder are satisfactorily bound together. Consequently, the probe electrode is composed of substantially pure carbon, which contributes to improving its mechanical strength. The probe electrode thus obtained exhibits a bending strength of greater than 20,000 gf/mm$^2$.

The probe electrode according to the present invention can be machine into any shape: needlelike, spherical, discoidal or bar-like, as occasion demands and depending on its use. Like the conventional platinum electrode, the probe electrode according to the present invention can minimize background current and, regardless of whether it is used on the positive or negative side, induce a good electrode reaction with excellent reproducibility. Furthermore, the probe electrode according to the present invention has a smaller background current than that of a conventional carbon electrode made of glassy carbon, pyroelectric graphite, carbon paste or the like.

Since the probe electrode according to the present invention contains no heavy metals such as Pb, Cd, As, Fe, Sb, Cr, Ca, Mg, Ti, Hg, Ba, etc., it is free from toxicity and capable of inducing an accurate electrode reaction.

Accordingly, the probe electrode according to the present invention is suitable for use in an electroanalysis or current-potential measuring apparatus; as an electrode for detecting electrode or battery reaction; or for liquid chromatography or electrophoresis. Moreover, it is usable as a probe sensor for environmental analysis or probe sensor electrode for detecting current and potential in food or a living body. Further, it is applicable to an article whose toxicity and safety are problematical as in the case of a toy.

The probe electrode according to the present invention, when its surface is coated with an enzyme, is also usable as a probe sensor for detecting current and potential in food or the living body. If it is deposited with an oxide, it is usable as an oxygen gas sensor.

Since the electrode has few gaps or pores therein, any substance sticking to the used electrode can easily be removed by cleansing and rubbing with a clean cloth or paper for the purpose of reuse.

FIG. 1 shows an example wherein the probe electrode according to the present invention is applied to an apparatus of a liquid separation effluent type for chromatography or electrophoresis. A probe electrode 1 in the form of a slender bar is supported with a tubular electrode holding fixture 2 in such a manner that its tip portion is exposed to an electrolyte 6 in an electrolytic bath 5. A reference electrode 3 and a counter electrode 4 are also immersed in the electrolyte 6.

Figure 2:
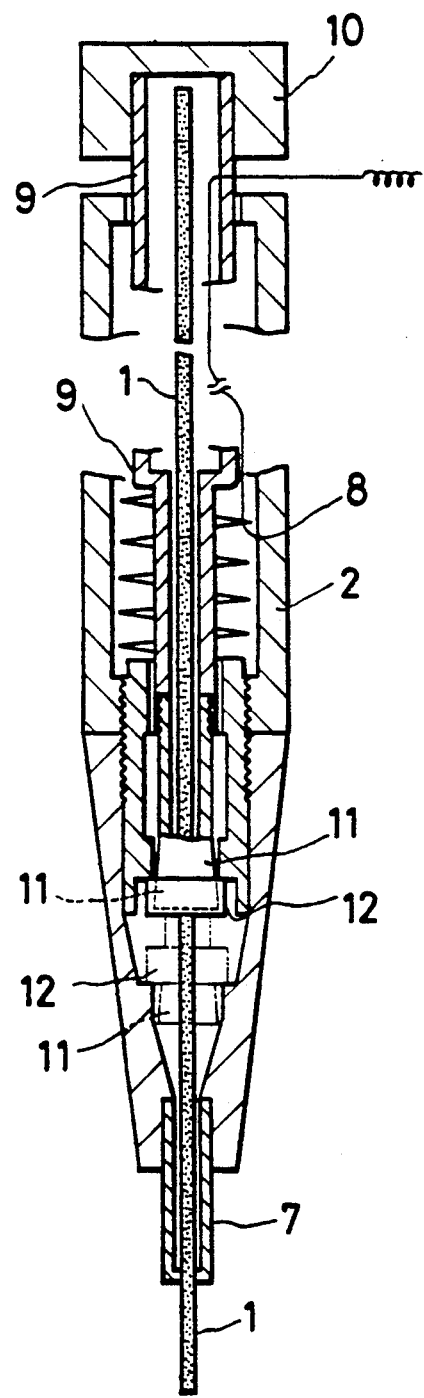
FIG. 2 is a sectional view illustrating a holding fixture of the electrode according to the present invention.

The tubular electrode holding fixture body 2 is, as shown in FIG. 2, arranged so that the electrode can be readily replaced by means of a built-in propulsion mechanism. More specifically, a slender pipe 7 having an inner diameter equal to the diameter of the electrode 1 to be held is fitted into the front end of the tubular body 2. In this tubular body 2, there is provided an inner cylinder 9 whose rear end is projected from the rear end portion of the body 2 and always biased backward by a spring 8. The rear end of the inner cylinder 9 is fitted with a knock member 10, whereas the front end of the inner cylinder 9 is fitted with a single-split grip member 11. A ring member 12 is fitted into the front end of the grip member 11. The slender bar electrode 1 is accommodated in the inner cylinder 9 and the slender pipe 7 is so inserted as to hold the front end of the electrode projected therefrom.

With this arrangement, the front end of the grip member 11 is covered with the ring member 12 since the inner cylinder 9 is kept biased backward by the spring 8 and the electrode 1 is fixedly gripped by the grip member 11.

The bar electrode 1 projected from the slender pipe 7 is severed using a suitable cutting means to provide a new electrode surface. When the knock member 10 is knocked then, the grip member 11 advances, thus releasing its front end from the ring member 12 mating therewith. The front end of the bar electrode 1 is projected from the slender pipe 7 by a length equivalent to one knock. When the knockout mechanism is released, the inner cylinder 9 is restored to the original position because of the spring 8, and the grip member 11 grips the bar electrode at a position equivalent to one knock operation to the rear.

A desired area of bar electrode 1 can thus be projected from the slender pipe 7 by knocking the knock member 10 the number of times required.

The mechanism for cutting the bar electrode 1 projected from the slender pipe 7 may be selected from among various kinds of cutting mechanisms.

Figure 3:
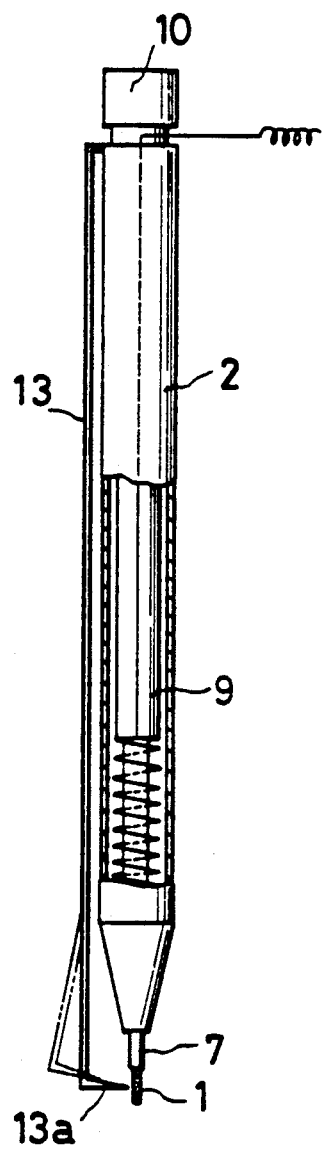
FIG. 3 is a side view including a partial sectional view of a cutter of the electrode according to the present invention.
Figure 4:
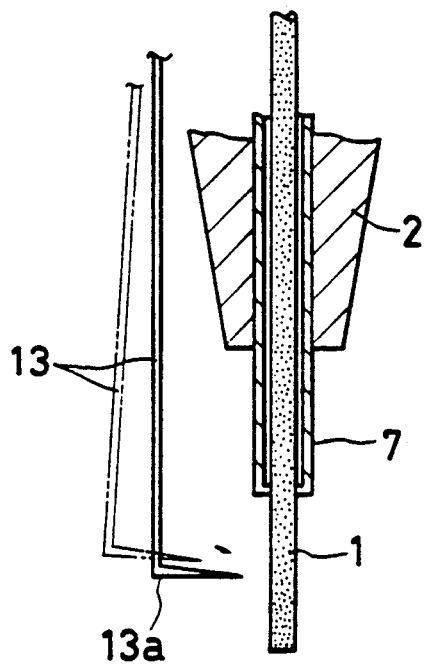
FIG. 4 is a diagram illustrating the cutter in operating condition of the electrode of FIG. 3.

FIGS. 3–6 are schematic views of such cutting mechanisms. The cutting mechanism illustrated in FIGS. 3, 4 is provided by securing to the periphery of the tubular body 2 the base of a cutting piece 13 formed of elastic metal or the like having an L-shaped cutting blade at its front end. In this case, the elasticity of the cutting piece 13 is utilized to cut the bar electrode 1 projected from the slender pipe 7.

Figure 5:
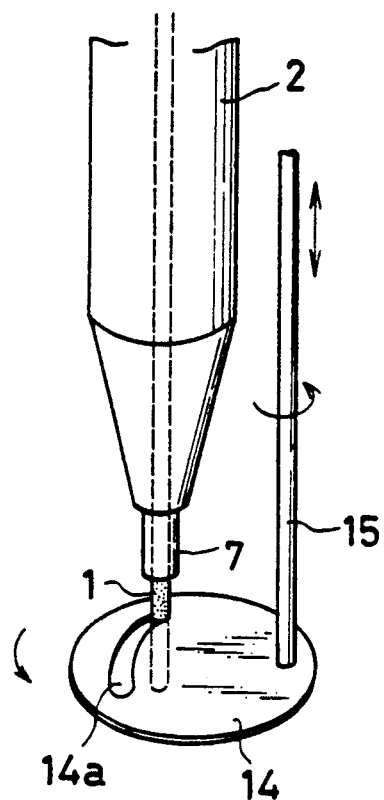
FIG. 5 is a perspective view of another cutter of the electrode according to the present invention.
Figure 6:
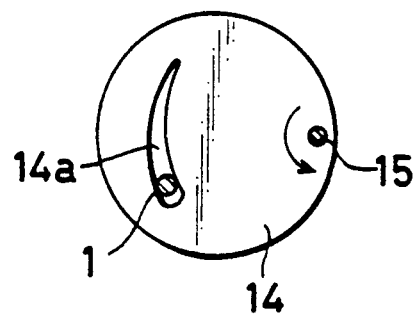
FIG. 6 is a diagram illustrating the cutter in operating condition of the electrode of FIG. 5.

The cutting mechanism illustrated in FIGS. 5, 6 is provided by arranging a rotary plate 14 having a tapered slot 14a in the front end portion of the carbon bar electrode 1. In this case, the bar electrode 1 projected from the slender pipe 7 is passed through the cutting slot 14a to an adequate extent and the bar electrode 1 is cut at the front end of the cutting slot 14 by turning the rotary plate 14. While the electrode is being used, the rotary plate 14 is removed from the bar electrode 1.

As set forth above, a new electrode surface can be readily supplied as in the case of the mercury electrode, since the extra thin bar electrode according to the present invention is held by the holding fixture of the electrode equipped with the electrode-propulsion and cutting mechanisms. If the electrode according to the present invention is projected into the fluid passageway of an electrochemical detector for chromatography, the ionic concentration of the fluid in contact with the electrode surface can readily be measured. When a different measurement is to be made, the electrode surface is wiped and treated at 2.0 V for a short time or the electrode portion projected into the passageway is cut in a proper way to extrude its new portion, so that reaction can take place on a new electrode surface.

A description will subsequently be given of embodiments of the present invention. However, it is to be understood that the present invention is not limited to the specific embodiments.

EXAMPLE 1

A mixture of 80 wt% natural graphite as a carbon material, 12 wt% vinyl acetate resin as an organic binder and 8 wt% spindle oil was sufficiently kneaded and subsequently molded into a slender bar 0.3 mm in diameter and 60 mm in length. Before being calcined, the slender bar was slowly heated up to 300° C. in air and heated up to 1,000° C. in an atmosphere of nitrogen gas.

Figure 7:
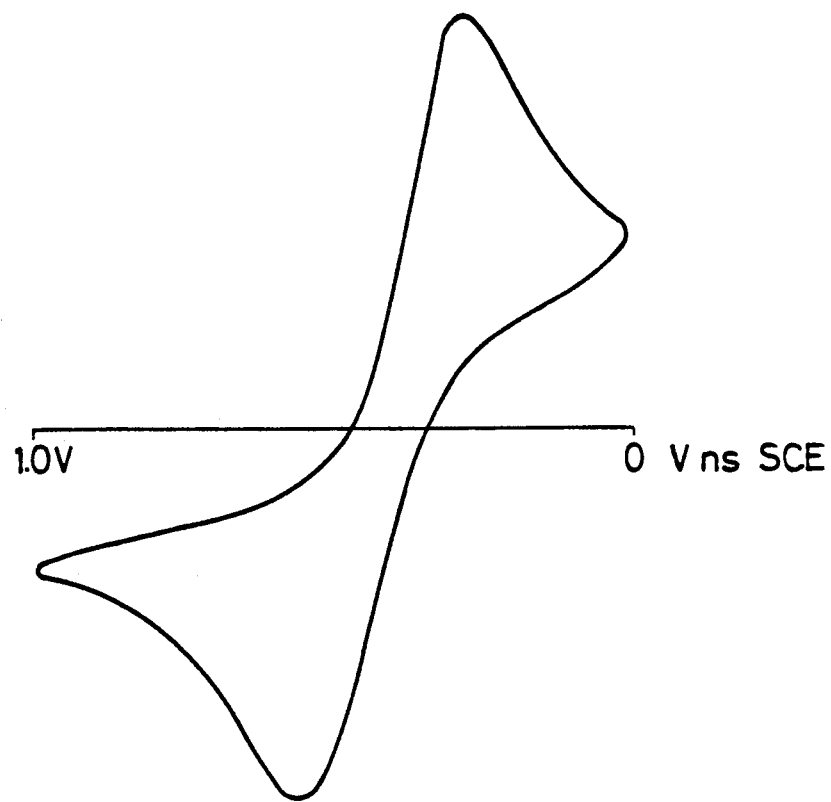
FIG. 7 is a cyclic voltammogram when iron ions in a hydrochloric acid solution are measured using the electrode according to the present invention.

The slender bar electrode thus prepared exhibited a bending strength of 20,000 gf/mm$^2$. This electrode was used as a working electrode and inserted, together with a reference electrode and a counter electrode, into a liquid fraction bath as an effluent after chromatographic separation and a cyclic voltammogram (C. V curve) was measured twice with an electrochemical measuring apparatus at a sweep rate of 500 mV/sec and a current sensitivity of 10 $\mu$A/V. Silver or silver chloride was used as the reference electrode, while as the counter electrode there was used a carbon electrode having a diameter of 0.9 mm and constituted identically to the aforesaid electrode. Qualitative determination of ions was conducted by reference to the peak and balanced potentials and the semiquantative determination thereof was made by reference to the peak height (C, V Fe-ion curve shown in FIG. 7).

A pulse voltammogram was obtained to make the quantitative determination of ions within the fraction. The use of a preset working curve makes it possible to make an accurate quantitative determination with the accuracy of $\pm 1\%$, though it takes a little more time.

Figure 8:
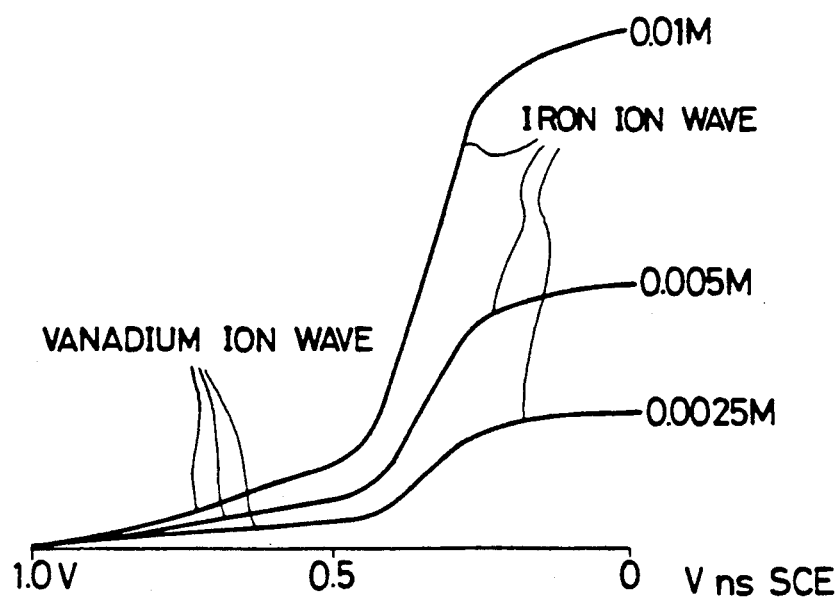
FIG. 8 is a pulse voltammogram when iron and vanadium ions in a hydrochloric acid solution are measured using the electrode according to the present invention.

In accordance with this method, the pulse voltammogram was measured with a polarographic analyzer fitted to the probe electrode, the analyzer having a sensitivity equivalent to 0.5 $\infty$A per volt, with the voltage changed at a rate of 5 mV/sec. FIG. 8 shows the results of Fe-ion analysis by means of the probe electrode.

EXAMPLE 2

A method of monitoring the charging and discharging conditions of a redox flow cell using the electrode according to the present invention will be described next.

Part of a positive electrolyte (of iron chloride $5 \times 10^{-3}$M) hydrochloric acid (1M) group) flowing from a tank into an electrolytic bath was diverged therefrom. A bar electrode as the probe electrode 0.5 mm in diameter was prepared by the method as explained in Example 1 and 5 mm of the electrode was immersed in the electrolyte thus led out. The ratio of $Fe^{3+}$ to $Fe^{2+}$ in the electrolyte was measured with the electrochemical measuring apparatus at a sweep rate of 500 mV/sec and a current sensitivity of 10 $\mu$A/V using an electrode of silver or silver chloride as the reference electrode.

Figure 9A:
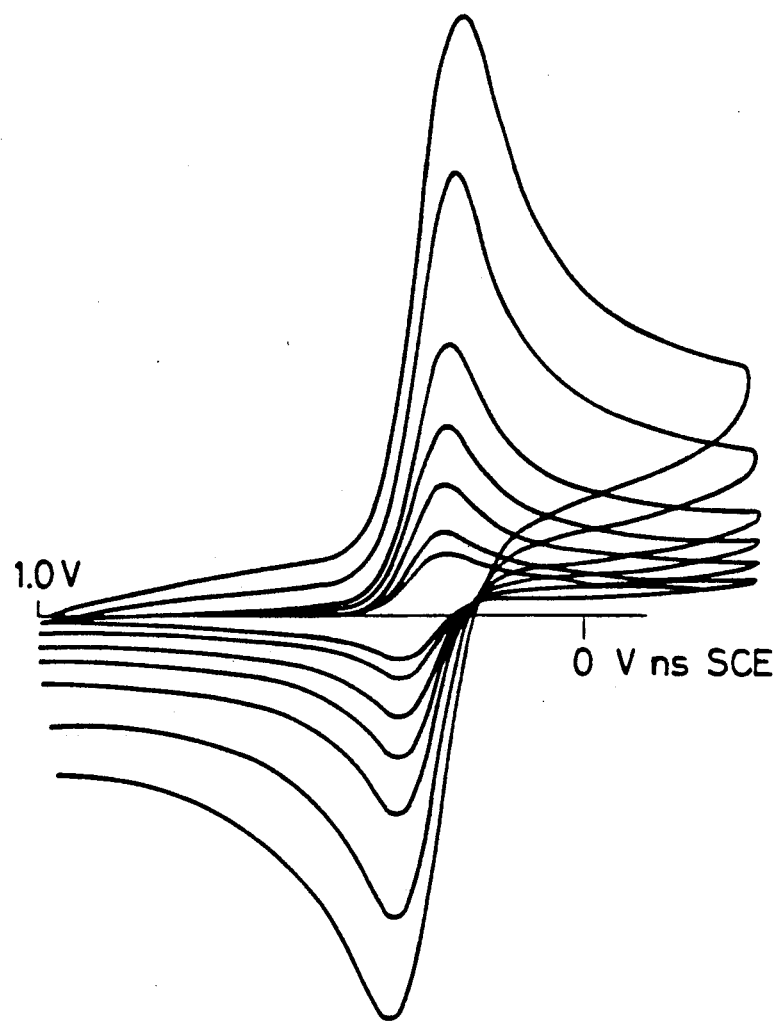
FIG. 9(*a*) is a cyclic voltammogram of ferric chloride in an electrolyte examined by the electrode according to the present invention.

The open circuit voltage was 0.45 V when the $Fe^{3+}$ to $Fe^{2+}$ ratio was 0.43 and the residual capacity was approximately 30%. The cyclic voltammogram of the iron chloride on the probe electrode was as shown in FIG. 9(a).

Figure 9B:
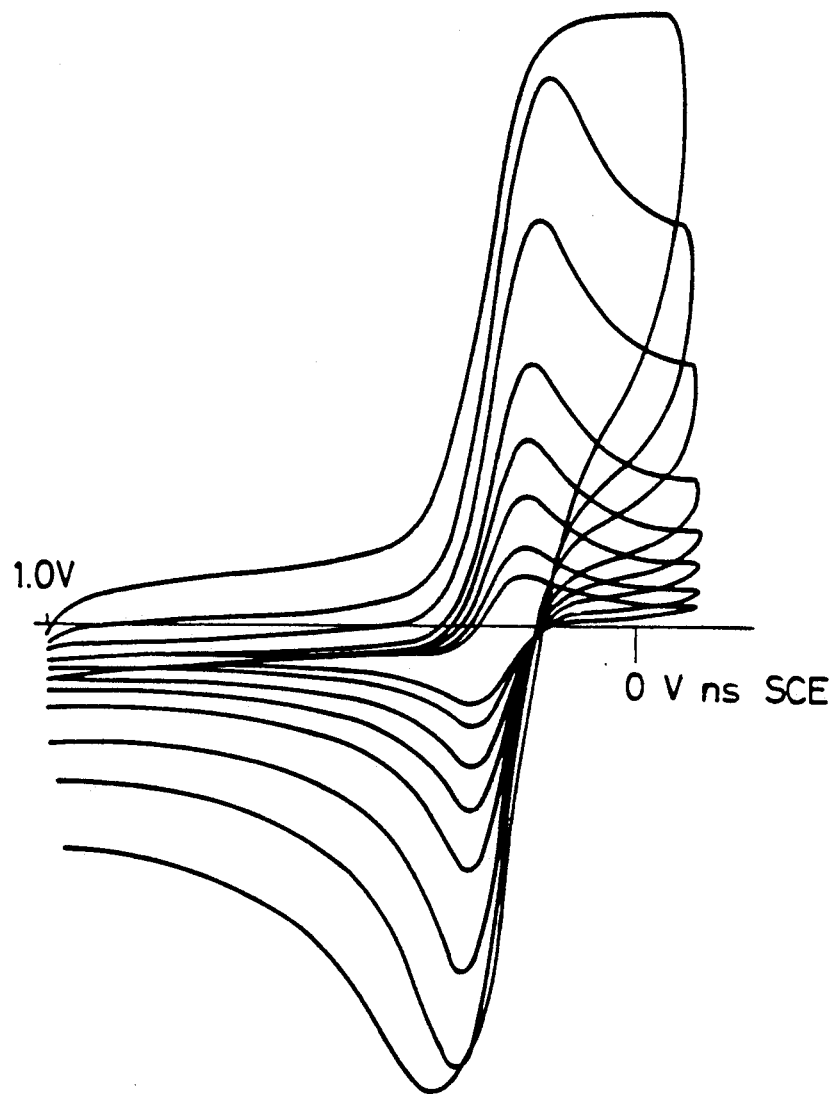

For the purpose of comparison, a platinum electrode 0.5 mm in diameter, instead of the carbon electrode, was employed to measure the cyclic voltammogram of the iron chloride. FIG. 9(b) shows the results obtained.

As is obvious from the aforesaid graphs, the two electrodes show behaviors quite similar to each other and the electrode according to the present invention has proved usable as a substitute for the conventional platinum electrode.

EXAMPLE 3

A small amount of blood (a few milliliters) put in a vessel having an inner capacity of 5 ml immediately after it was collected. A cylindrical electrode prepared under conditions similar to those of Example 1, together with a reference electrode (saturated calomel electrode) 1 mm in diameter and a cylindrical counter electrode 0.9 mm in diameter, was immersed in the blood, the probe electrode being 0.3 mm in both diameter and length.

Voltammogram measurement by means of a polarographic analyzer showed the redox potential of hemoglobin within the blood to be 0.17 V/pH 6 and 0.15 V/pH 7 with respect to the reference electrode. These values were almost identical to those obtained with a platinum electrode.

Since the redox potential of hemoglobin in the blood varies with pH, the measurement of the potential is important in estimating the blood condition in the body. In view of this, the electrode according to the present invention ensures that reliable measurement results are readily obtained.

EXAMPLE 4

A probe electrode 0.5 mm in diameter was prepared under the conditions similar to those of Example 1 and the electrode, together with a platinum electrode as the counter electrode and a fine calomel electrode as the reference electrode, was thrust into a segment of a tangerine. Then the content of ascorbic acid (vitamin C) contained therein was measured with a polarographic analyzer at a sweep rate of 500 mV/sec and a current sensitivity of 10 $\mu$A/V.

The three electrodes were subsequently pulled out of the segment and the probe electrode was washed with pure water and cleaned by slightly rubbing its surface with soft paper. The electrode, together with the counter and reference electrodes, was thrust into another kind of tangerine to measure the content of ascorbic acid. The electrode was again washed and wiped in the same manner and thrust into a grapefruit, simultaneously with a solution of vitamin C (concentration of 1%) for reference, to semiquantitatively determined the content of ascorbic acid.

Figure 10:
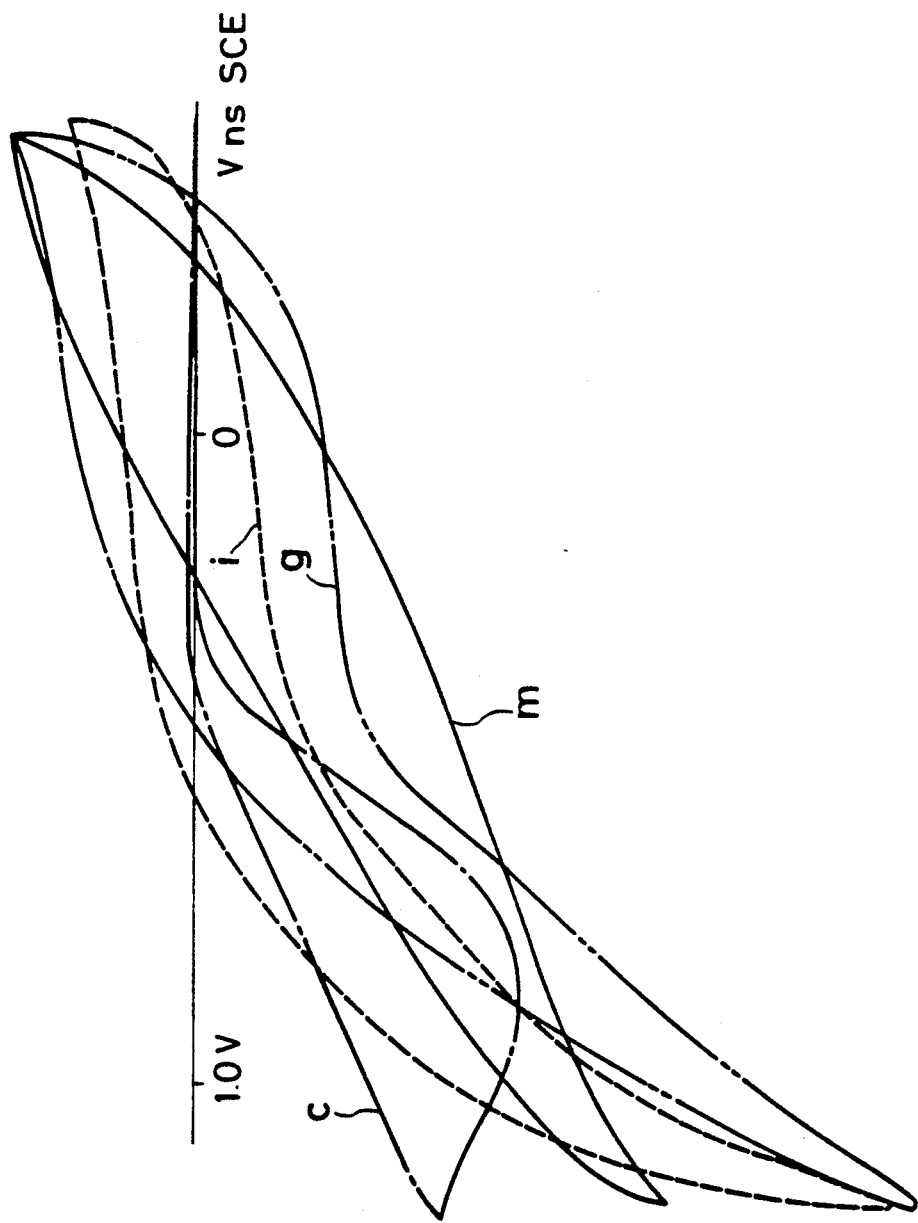
FIG. 10 is a cyclic voltammogram when ascorbic acid of citrus fruits is examined by the electrode according to the present invention.

FIG. 10 shows the measurement results. In FIG. 9, the curve m represents the cyclic voltammogram of the tangerine, g the grapefruit, i another tangerine, and c the vitamin C.

The electrode according to the present invention can be used to examine a plurality of samples quite easily only by wiping the surface thereof. It can also be employed for quantitative determination using a working curve.

EXAMPLE 5

A thin bar electrode was prepared under conditions similar to those of Example 1. The electrode was, as shown in FIG. 2, supported by an electrode holding fixture of a knock propulsion type in such a manner that it was projected by 2 mm from the front end thereof. The electrode thus projected was immersed in an electrolyte having an iron (III) ion concentration of 0.01 M. A carbon electrode 2 mm in diameter and a saturated calomel electrode (SCE) were employed as the counter and reference electrodes, respectively. Then the peak current value of the iron ions located on the SCE at a level of 0.25 V on the voltammogram was read out while the voltage was changed at a sweep rate of 200 mV/sec.

The propulsion mechanism of the holding fixture was operated to change the length of the electrode projected therefrom to 3.5, 7.5, 10 mm and the iron ions were measured under the same conditions.

The table below shows the results of measurement.

| Length of Electrode (mm): | Peak Current Value (mA): |
| --- | --- |
| 2 | 0.06 |
| 3 | 0.09 |
| 5 | 0.15 |
| 7.5 | 0.23 |
| 10 | 0.30 |

The peak current value (the amount of current) is proportional to the surface area of the electrode and, as is obvious from the table above, the peak current value increases in proportion to the length of the electrode projected. Accordingly, the concentration of iron ions can be measured in an extremely simple way by means of the electrode according to the present invention.

What is claimed is:

1. A probe electrode comprising substantially 100% of carbon prepared by kneading a mixture of 75–80 wt % carbon material, a 10–14 wt % organic binder, and 7–9 wt % mineral oil, calcining said mixture to form a calcined mixture and impregnating mineral oil into said calcined mixture to fill pores.

2. A probe electrode as claimed in claim 1, wherein said carbon material is graphite containing no heavy metals.

3. A probe electrode as claimed in claim 1, wherein said organic binder is selected from the group consisting of ineyl acetate resin, epoxy resin and phenol resin.

4. A probe electrode as claimed in claim 1, wherein said mineral oil impregnated into said calcined mixture is silicone or VASELINE.

5. A probe electrode as claimed in claim 1, wherein said probe electrode has a diameter in the range of 0.3 to 0.5 mm.

6. A probe electrode as claimed in claim 5, wherein said probe electrode has a bending strength of more than 20,000 gf/mm$^2$.

7. A probe electrode comprising substantially 100% of carbon prepared by kneading a mixture of a 75–80 wt % carbon material, a 10–14 wt % organic binder, and 7–9 wt % mineral oil, calcining said mixture to form a calcined mixture and impregnating mineral oil into said calcined mixture to fill pores and make said calcined mixture impenetrable to liquids.

8. A probe electrode as claimed din claim 7, wherein said carbon material is graphite containing no heavy metals.

9. A probe electrode as claimed in claim 7, wherein said organic binder is selected from the group consisting of vinyl acetate resin, epoxy resin and phenol resin.

10. A probe electrode as claimed in claim 7, wherein said mineral oil impregnated into said calcined mixture is silicone or VASELINE.

11. A probe electrode as claimed in claim 7, wherein said probe electrode has a diameter in the range of 0.3 to 0.5 mm.

12. A probe electrode as claimed in claim 11, wherein said probe electrode has a bending strength of more than 20,000 gf/mm$^2$.

13. A probe electrode comprising substantially 100% of carbon prepared by kneading a mixture of a 75-80 wt % carbon material, a 10-14 wt % organic binder, and 7-9 wt % mineral oil, calcining said mixture to form a calcined mixture and impregnating mineral oil into said calcined mixture to fill pores whereby said electrode prevents an electrolyte form entering therein.

14. A probe electrode as claimed in claim 13, wherein said carbon material is graphite containing no heavy metals.

15. A probe electrode as claimed in claim 13, wherein said organic binder is selected for the group consisting of vinyl acetate resin, epoxy resin and phenol resin.

16. A probe electrode as claimed in claim 13, wherein said mineral oil impregnated into said calcined mixture is silicone or VASELINE.

17. A probe electrode as claimed din claim 13, wherein said probe electrode has a diameter in the range of 0.3 to 0.5 mm.

18. A probe electrode as claimed in claim 17, wherein said probe electrode has a bending strength of more than 20,000 gf/mm$^2$.

* * * * *